US008404701B2

(12) United States Patent
Chase et al.

(10) Patent No.: US 8,404,701 B2
(45) Date of Patent: Mar. 26, 2013

(54) USE AND COMPOSITION FOR TREATING DEMENTIA

(75) Inventors: Thomas N. Chase, Washington, DC (US); Kathleen E. Clarence-Smith, Washington, DC (US)

(73) Assignee: Chase Pharmaceuticals Corporation, Washington, DC (US)

( * ) Notice: Subject to any disclaimer, the term of this patent is extended or adjusted under 35 U.S.C. 154(b) by 0 days.

(21) Appl. No.: 12/934,140

(22) PCT Filed: Mar. 17, 2009

(86) PCT No.: PCT/US2009/001662
§ 371 (c)(1),
(2), (4) Date: Sep. 23, 2010

(87) PCT Pub. No.: WO2009/120277
PCT Pub. Date: Oct. 1, 2009

(65) Prior Publication Data
US 2011/0021503 A1 Jan. 27, 2011

(30) Foreign Application Priority Data
Mar. 27, 2008 (EP) .................................. 08005750

(51) Int. Cl.
*A01N 43/42* (2006.01)
*A01N 43/36* (2006.01)
*A61K 31/44* (2006.01)
*A61K 31/40* (2006.01)
(52) U.S. Cl. ....................................... 514/278; 514/424
(58) Field of Classification Search .................... None
See application file for complete search history.

(56) References Cited

U.S. PATENT DOCUMENTS

| 2005/0010259 | A1* | 1/2005 | Gerber ............................. 607/39 |
| 2005/0065176 | A1 | 3/2005 | Field et al. |
| 2006/0293356 | A1 | 12/2006 | Aberg |
| 2008/0114014 | A1* | 5/2008 | Rich ............................. 514/278 |

FOREIGN PATENT DOCUMENTS

| WO | WO 2008/033299 A | 3/2008 |
| WO | WO 2008033299 A2 * | 3/2008 |

OTHER PUBLICATIONS

Aricept(R) (Donepezil Hydrochloride Tablets) NDA 20-690/ S-026 (no date).*
Faber et al., Enhancing the Tolerability of Tacrine With Propantheline, Am J Pyschiatry, 156:1, Jan. 1999.*
Glycopyrrolate tablet (West-ward Pharmaceutical Corp) Human Prescription Drug Label, available at http://dailymed.nlm.nih.gov/dailymed/drugInfo.cfm?id=65407.*
Suzuki, M. et al., Effect of antimuscarinic drugs used for overactive bladder on learning in a rat passive avoidance response test, Eur. J. Pharm., (Feb. 2007) vol. 557, Issues 2-3, pp. 154-158.*
U.S. Appl. No. 12/880,395, filed Sep. 2010, Chase, T.*
Fu et al, "Propantheline Attenuates the Peripheral Side Effects of Donepezil without Affecting its Antiamnestic Properties in Cerebral Ischemic Mice", Journal of Health Science, 54(4) 409-415 (2008).
Zhang et al, "Peripheral Cholinoceptor Antagonist Anisodamine Counteracts Cholinergic Adverse Effects and Facilitates Cognitive Amelioration of Rivastigmine", J Neural Transm. Dec. 2009; 116(12):1643-9.
International Search Report for PCT/US2009/001662, mailed Jun. 23, 2009.
Siegler et al, "Treatment of Urinary Incontinence with . . . ", Clinical Pharmacology & Therapeutics, vol. 75, No. 5, May 2004; pp. 484-488, XP009102926.
Anghelescu et al, "[Acetylcholinesterase inhibitors for dementia—an update]" MMW Fortschritte der Medizin May 21, 2007, vol. 149, Suppl 2, pp. 76-78, XP009102887.
Takeda et al, $33^{rd}$ Annu Meet Int. Continence Soc (Oct. 5-9, Florence) 2003, Abst. 166, XP 009102822.
Scheife et al, "Central Nervous System Safety of Anticholinergic Drugs . . . ", Clinical Therapeutics, Excerpta Medica, Princeton, NJ, vol. 27, No. 2, Feb. 1, 2005, pp. 144-153, XP004874590.
Cappon et al, "Tolterodine does not affect memory assessed . . . ", European Journal of Pharmacology, vol. 579, No. 1-3, Jan. 2008, pp. 225-228, XP002489794.
Madersbacher, "[Oral anticholinergics in overactive bladder]" Der Urologe. Ausg. A Jul. 2006, vol. 45, No. 7, Jul. 2006, pp. 830-834, XP002489795.
Schultz-Lampel, "Bladder disorders in patients with dementia . . . ", Urologe A, vol. 42, No. 12, 2003, pp. 1579-1587, XP002489800.
Faber et al, "Enhancing the tolerability of tacrine with propantheline", The American Journal of Psychiatry, Jan. 1999 Lnked—PubMed: 9892315, vol. 156, No. 1, Jan. 1999, p. 156, XP002631460.

* cited by examiner

Primary Examiner — Shengjun Wang
Assistant Examiner — Svetlana M Ivanova
(74) Attorney, Agent, or Firm — Sughrue Mion, PLLC

(57) ABSTRACT

There is described a method for increasing the maximal tolerated dose and thus the efficacy of an acetyl choline esterase inhibitor (AChEI) in a patient suffering from an Alzheimer type dementia by decreasing concomitant adverse effects by administration of said AChEI in combination with a non-selective, peripheral anticholinergic agent, whereby an enhanced acetyl choline esterase inhibition in the CNS of said patient is achieved and alleviation of the symptoms of Alzheimer type dementia in said patient is thereby improved to a greater extent. The use of a non-selective, peripheral anticholinergic agent (nsPAChA) for the preparation of a pharmaceutical composition for increasing the maximal tolerated dose and thus the efficacy of an acetyl choline esterase inhibitor (AChEI) in a patient suffering from an Alzheimer type dementia and pharmaceutical compositions comprising a non-selective peripheral anticholinergic agent of formula II as illustrated in the description and an acetylcholine esterase inhibitor are also described.

13 Claims, No Drawings

USE AND COMPOSITION FOR TREATING DEMENTIA

This application is the U.S. national phase of International Application No. PCT/US2009/001662 filed 17 Mar. 2009, and claims priority to EP Application No. 08005750.8 filed 27 Mar. 2008, the entire contents of each of which is hereby incorporated by reference.

FIELD OF THE INVENTION

This invention concerns a method for enhancing the maximal efficacy and maximal tolerated dose of an acetyl choline esterase inhibitor in a patient suffering from dementia of the Alzheimer type by combining said acetyl choline esterase inhibitor with a non-selective, peripheral anticholinergic agent, or the use of a non-selective, peripheral anticholinergic agent (nsPAChA) for the preparation of pharmaceutical compositions for the treatment of Alzheimer type dementias in combination with an acetyl choline esterase inhibitor (AChEI). The invention also concerns pharmaceutical compositions comprising a non-selective, peripheral anticholinergic agent consisting of a quaternary ammonium or a sulfonium compound or of a non-quaternary ammonium compound selected from the group consisting of solifenacin, propiverine, oxyphencyclimine and tolterodine in association with an acetylcholine esterase inhibitor for increasing and prolonging the efficacy and decreasing the toxicity of conventional cholinomimetic treatments such as treatments for dementias in diseases of the Alzheimer type.

DEFINITIONS

"AChEI(s)": Acetyl Choline Esterase Inhibitor(s).
"NsPAChA(s)": non-selective, peripheral AntiCholinergic Agent(s).
"Non selective": referred to nsPAChAs, applies to anticholinergic agents exhibiting inhibitory activity broadly across the various subtypes of muscarinic M-receptors, namely the M1-M5 receptors, as currently identified.
"Peripheral": referred to nsPAChAs, applies to anticholinergics that are largely unable (have a limited ability) to enter the central nervous system following systemic administration and thus do not affect brain function to a clinically appreciable degree. These drugs can include both quaternary and tertiary ammonium anticholinergic agents, especially those having low lipid solubility.
"CNS": Central Nervous System.
"CSF": Cerebrospinal Fluid.
"PNS": Peripheral Nervous System.
"IR": Immediate Release of the active ingredient from a composition.
"ER": Extended Release of the active ingredient from a composition.

BACKGROUND OF THE INVENTION

Dementias of the Alzheimer type include, but are not limited to Alzheimer's disease, Parkinson's disease dementia, and related maladies in humans involving cognitive and behavioral dysfunction such as Lewy body dementia. Most are chronic neurodegenerative disorders of the human central nervous system (CNS) characterized by progressive cognitive impairment, a variety of neurobehavioral and/or neuropsychiatric disturbances, and restrictions in activities of daily living.

Alzheimer's disease is the most common form of dementia. Prevalence studies indicated that in 2000 there were about 25 million persons with Alzheimer's disease worldwide and this number is expected to increase to 114 million by 2050 unless an effective preventive or neuroprotective therapy emerges. Onset usually occurs in those over age 65. Clinical signs include progressive cognitive loss and other associated neurobehavioral disabilities together with a declining capability of performing the activities of daily living.

The basic cause of sporadic Alzheimer's disease is not known, probably because the disease is heterogeneous and involves age-related changes together with a complex interaction of genetic and environmental risk factors. Current hypotheses advanced to explain the pathophysiology of Alzheimer's disease center on the putative deleterious effects of the two misfolded and aggregated proteins, extracellular beta amyloid and intracellular tau. Presumably, as a consequence of the selective neurodegenerative process, the synthesis of the neurotransmitter acetylcholine declines. This reduction undoubtedly interferes with normal synaptic transmission in brain. Drugs that act to correct the acetylcholine deficiency thus constitute the mainstay of current therapy.

Dementias of the Alzheimer type also include cognitive impairments associated with Parkinson's disease. One example is Parkinson's disease dementia, also a chronic progressive CNS degenerative disorder with relatively late life onset. Parkinson's disease itself primarily affects motor function. But secondary symptoms include cognitive deterioration, especially deficits in executive function.

Another dementia of the Alzheimer type that is commonly linked to Parkinson's disease is known as dementia with Lewy bodies or Lewy body dementia. Although Lewy body dementia is now generally regarded as a separate disease, differentiation from Alzheimer's disease and from Parkinson's disease dementia may be clinically challenging. Lewy body dementia thus tends to be under-diagnosed or misdiagnosed as Alzheimer's disease or Parkinson's disease dementia. The clinical presentation of Lewy body dementia is typically one of cortical and subcortical cognitive impairment, with visuospatial and executive dysfunction more pronounced than in Alzheimer's disease. Core clinical features of Lewy body dementia, in addition to parkinsonism, are cognitive decline plus fluctuations in attention and recurrent visual hallucinations.

Both Parkinson's disease dementia and Lewy body dementia are characterized neuropathologically by the presence of cortical Lewy body pathology and synuclein protein deposition. Genetic factors appear to play a role in pathogenesis. Not surprisingly, the pathology of Parkinson's disease dementia and Lewy body dementia is heterogeneous and overlapping, often intermixed with changes of the Alzheimer and vascular types. A reduction in brain acetylcholine-mediated neurotransmission has been linked to the primary clinical abnormalities found in both these disorders and drugs acting to stimulate cholinergic transmission now constitute the main approach to therapy.

In addition to the aforementioned disorders, the off label administration of drugs that augment CNS cholinergic transmission for various other cognitive disorders is widespread. Some of this use involves cognitive disorders for which relatively little clear evidence of cholinergic dysfunction currently exists. Nevertheless, an increasing number of clinical studies now support a rational extension of AChEI treatment to various additional disorders of cognitive function, including but not limited to, vascular dementia, Down syndrome, traumatic brain injury and mild cognitive impairment.

As noted above, reduced levels of neurotransmitters including acetylcholine have been reported in dementias of the Alzheimer type and related disorders. In particular, a deficit in acetylcholine-mediated transmission is thought to contribute to the cognitive and certain of the neurobehavioral abnormalities associated with these disorders. Accordingly, drugs known to augment cholinergic transmission in the CNS are widely used in therapy.

AChEIs are now part of the standard care for patients suffering from a dementia of the Alzheimer type and are widely used off label for various other chronic progressive disorders of cognitive function. AChEIs have the enhancement of acetylcholine-mediated neurotransmission as a general mechanism of action. All act in the human CNS to increase and prolong the availability of acetylcholine by inhibiting its degradatory enzyme acetylcholinesterase. Four AChEIs have been approved by the U.S. FDA for the treatment of Alzheimer's disease and for Parkinson's disease dementia: tacrine, donepezil [Aricept®], rivastigmine [Exelon®] and galantamine [Razadyne®]. AChEIs are available in various formulations including immediate release forms such as tablets, capsules and solutions as well as rapid dissolving and extended release forms for oral administration as well as those for parenteral (eg transdermal) administration.

For example, tacrine is presented in capsules containing 10, 20, 30, 40 mg/capsule and was used at recommended daily dosages of from 40 to 160 mg (divided into 4 doses); donepezil is presented, as hydrochloride, in orally disintegrating tablets containing 5, 10 mg/tablet and is used at recommended daily dosages of from 5 to 10 mg; rivastigmine is presented in capsules containing the tartrate in amounts corresponding to 1.5, 3, 4.5 and 6 mg of rivastigmine base, as oral solution containing the tartrate corresponding to 2 mg of rivastigmine base and in form of a transdermal patch releasing rivastigmine at 4.6 mg/24 hours or 9.5 mg/24 hours, the recommended daily dosage for the IR forms being of from 6 to 12 mg, divided into 2 doses and the maximal recommended patch dose being 9.5 mg/24 hours; and galantamine is available in ER capsules of 8 mg, 16 mg and 24 mg containing 5.126, 10.253, and 15.379 mg of galantamine hydrobromide, respectively, corresponding to 4 mg, 8 mg and 12 mg, respectively, of galantamine base and as a 4 mg/mL oral solution, the recommended daily dosage being from 16 mg to 32 mg, in the United States of America the maximum recommended daily dose having been reduced to 24 mg divided into 2 doses.

A brief review of the efficacy of the AChEIs rivastigmine, donepezil and galantamine for the treatment of dementia diseases, by Angelescu et al., has been published in MMW-Fortschr. Med. Sonderheit, 2007, 149, 76-78 ("Angelescu 2007").

Other AChEIs, in particular tacrine analogs, such as ipidacrine; phenserine and their analogs; icopezil; and zanapezil are under evaluation.

AChEIs vary in their pharmacological profiles and in their affinities for acetylcholinesterase and butyrylcholinesterase. Donepezil and galantamine are 1000- and 50-fold, respectively, more selective for acetylcholinesterase than for butyrylcholinesterase, whereas rivastigmine inhibits both enzymes with similar affinity (Thomsen et al., Life Scie. 1990, 46, 1553-58) and certain analogs of phenserine are more selective for butyrylcholinesterase (see for example Qian-sheng Yu et al., J Med Chem, 1997, 40(18),2895-2898 and U.S. Pat. No. 6,683,105).

Augmentation of cholinergic transmission in the CNS by currently available AChEIs confers therapeutic benefit to patients with Alzheimer type dementias. Therapeutic efficacy can be measured by the degree of improvement in cognitive dysfunction and other neurobehavioral abnormalities associated with these disorders using standardized scales.

Unfortunately, however, none of the currently available medications offer more than modest clinical benefit for some patients suffering from any of the aforementioned dementing disorders, even when these medications are administered at their maximum safe and tolerated doses. This is the first problem limiting the success of current AChEI therapy of Alzheimer type dementias.

Carefully conducted clinical trials of donepezil (Rogers et al., Neurology 1998, 50, 136-45; Winblad et al. Neurology. 2001 Aug. 14; 57(3):489-95), rivastigimine (Rösler et al., Brit. Med. J. 1999, 318, 633-38; Farlow et al. Eur. Neurol., 2000, 44, 236-41) and galantamine (Raskind et al., Neurology, 2000, 54, 2261-68; Tariot et al., Neurology, 2000, 54, 2269-76) in patients with dementias of the Alzheimer type demonstrated small, but statistically significant, benefits on cognitive and global measures relevant to dementia. The magnitude of the effect in pivotal clinical trials was on the order of a 2.8 point improvement on the 70-point cognitive subscale of the Alzheimer's Disease Assessment Scale (ADAS-Cog), or 1-1.5 point improvement on the 30-point Mini-Mental Status Examination (MMSE) compared to placebo over six months. Differences in global measures assessed by the 7-point Clinician Interview-Based Impression of Change scale (CIBIC) were on the order of 0.3-0.5 points in patients receiving an AChEI compared to those receiving placebo. Efficacy was similar for the three commonly used AChEIs. AChEIs also appear to have a beneficial effect on the behavioral and neuropsychiatric symptoms in patients with Alzheimer type dementias.

A second problem limiting the success of current AChEI therapy of Alzheimer type dementias is that, even at recommended amounts, all these drugs produce dose limiting adverse reactions, mainly by over-stimulating peripheral cholinergic receptors of the muscarinic type. As a result, signs and symptoms of untoward gastrointestinal, pulmonary, cardiovascular, urinary, and other systems dysfunction occur. These side effects commonly include, for the aforementioned AChEIs tacrine, donepezil, rivastigmine and galantamine: anorexia, nausea, vomiting, diarrhea, abdominal pain, weight loss; increased bronchial secretions, dyspnea, bronchoconstriction and bronchospasm; bradycardia, supraventricular cardiac conduction abnormalities, vasodilation, hypotension, dizziness and syncope; urinary bladder spasm, increased urinary frequency, and incontinence; flushing and diaphoresis; fatigue, headache, lacrymation, miosis, and loss of binocular vision (Physicians Desk Reference 2008, Thomson PDR, Montvale, N.J.).

The most frequently reported adverse effects of rivastigmine, for example, are gastrointestinal, especially nausea. About half of patients who take this drug in the recommended therapeutic oral dose range of 6-12 mg/day become nauseated and about one-third vomit at least once. Vomiting was severe in 2% of rivastigmine-treated patients and was mild or moderate in 14%. Five percent of patients discontinued rivastigmine because of vomiting, compared to less than 1% on placebo. A loss of appetite was reported by 17% of patients, and weight declined in 25% during rivastigmine therapy (averaging 7 to 10 pounds). Presumably, the drug-induced anorexia, nausea and vomiting contribute to the observed weight loss. These untoward gastrointestinal effects, as well as others occurring with AChEI treatment, make it difficult to increase rivastigmine dosage above 6 mg daily in most patients.

Adverse events attending the use of AChEIs appear to primarily reflect the excessive stimulation of peripheral cholinergic receptors, especially those of the muscarinic type (mAChRs). Five subtypes of muscarinic receptors, M1 through M5, have now been identified. Ongoing research has begun to map the distribution and physiologic role of these receptors as well as determine the binding affinity of drugs to them. For example, M1 receptors are found in sympathetic postganglionic neurons (autonomic ganglia), in gastric tissue and in the myenteric plexus; they are involved in secretions from salivary glands and the gastrointestinal tract. M2 receptors are present in cardiac and smooth muscle and have been implicated in the regulation of contractile forces of the atrial cardiac muscle and the conduction velocity of the atrioventricular node and thus heart rate. M2 receptors are also present on gastrointestinal smooth muscle as well as on detrusor smooth muscle cells and other structures within the bladder wall. M3 receptors are the predominant muscarinic receptor subtype mediating contraction of the stomach fundus, urinary bladder, and trachea. They are also expressed on glandular cells including gastric parietal cells and on vascular smooth muscle as well as detrusor smooth muscle and other structures within the bladder wall. M3 receptors are involved in exocrine gland secretion, smooth muscle contractility, emesis, pupil dilatation, food intake and weight gain.

The characterization of muscarinic receptor subtypes remains incomplete, especially in relation to the more recently identified M4 and M5 receptors, and now appears far more complex than originally envisioned. The precise relation between a particular muscarinic receptor subtype and a specific bodily function, or a particular symptom of excessive stimulation is not yet fully known. Similarly, many drugs remain incompletely characterized with respect to their muscarinic receptor binding profiles. Nevertheless, the available evidence indicates that many of the adverse events occurring in association with the administration of recommended dose levels of any of the currently used AChEIs can be linked to stimulation of the currently recognized peripheral muscarinic receptor subtypes. Accordingly, muscarinic antagonists that bind with the highest affinity to those muscarinic receptor subtypes that give rise to the most severe AChEI-induced adverse effects in any particular human subject might prove optimal for that individual. But as a practical matter, since acetylcholine interacts with all muscarinic receptor subtypes, non-subtype-selective muscarinic antagonists are generally preferred as the best approach to clinical therapy.

Adverse events significantly reduce the safety and tolerability of AChEI therapy. Attempts to limit them in clinical practice now rely on initiating treatment with a low dose and then escalating the dose slowly. Nevertheless, in current clinical practice, AChEI dosage is guided mainly by side effects and not by therapeutic effects in contrast to most drugs in the treatment of neuropsychiatric disease. The administration of higher doses than recommended doses tends to increase the frequency and severity of these side effects as well as introduce additional kinds of adverse reactions. These include those generally found with high dose administration of cholinomimetics. In view of the frequency and potential severity of these high dose adverse effects, maximum recommended oral doses of AChEIs are rarely intentionally exceeded in clinical practice.

The degree to which AChEIs can attenuate the activity of this enzyme in the CNS can be estimated by assays of AChE activity and related protein levels in the CSF. It is reported that recommended maximal dose levels of these drugs typically achieve only about 45% AChEI inhibition (without a concomitant increase in AChE protein levels) in the CNS of Alzheimer disease patients (Brannan S et al. ACNP 46th Annual Meeting, Program No. 4. Boca Raton Fla., Dec. 10, 2007—"Brannan 2007"; Farlow M et al AAN Poster 2008; Davidsson P et al Neurosci Lett 2001; 300:157-60; Amici S et al Mech Ageing Dev 2001; 122:2057-62) and that inhibition of AChEI activity and cognitive improvement are significantly correlated (Giacobini et al. J Neural Transm. 2002 July; 109(7-8):1053-65; Darreh-Shori T et al, J Neural Trans 2006; 113:1791-801) and that, ordinarily, a higher degree of enzyme blockade must be attained for maximum functional effect (Jann et al., Clin Pharmacokinet. 2002; 41(10):719-39—"Jann 2002").

On the other hand, doubling the dose of rivastigmine, which became clinically practical when AChEI administration by immediate release tablets was replaced by skin patches, which diminished side effects by blunting peak blood levels, significantly increased the amount of cognitive improvement in patients with Alzheimer's disease without increasing side effects.

By virtue of being dose limiting, these adverse effects also constrain the efficacy of AChEI therapy. Studies in animal models of human cognitive dysfunction indicate a direct dose-response relation between the amount of acetyl choline esterase inhibition and the degree of cognitive improvement (Bennett B M et al., Neuropsychopharmacology. 2007 March; 32(3):505-13). Similar conclusions have been drawn regarding AChEI effects on cognitive and behavioral symptoms in human patients with Alzheimer's disease (Jann 2002; Winblad B, Cummings J, Andreasen N, Grossberg G, Onofrj M, Sadowsky C, Zechner S, Nagel J, Lane R. Int J Geriatr Psychiatry. 2007 May; 22(5):456-67).

PRIOR ART

A benefit of alleviating the side effects of an AChEI was described in a report of four patients in whom the treatment of Alzheimer's disease with the AChEI tacrine was complicated by peripheral cholinergic gastrointestinal side effects, especially cramping, nausea, vomiting and diarrhea (Faber et al. Am J Psychiatry 156:1, 1999, page 156—"Faber 1999"). These adverse events were ameliorated by the adjunctive use of the anticholinergic propantheline (Pro-Banthine®) at 7.5 to 15 mg taken four times a day. Based on these results, the authors recommended adjunctive use of propantheline in patients with untoward gastrointestinal cholinergic effects from cholinesterase inhibitors.

Nevertheless, the aforementioned application of the general concept for improving the treatment of dementias of the Alzheimer type provides only limited benefit to patients suffering from these disorders. Propantheline has disadvantages that preclude general clinical usefulness in this application. This anticholinergic and others of its type, such as methantheline bromide thus fall short of perfecting the actualization of the therapeutic potential of this approach. There are four main problems regarding the anticholinergic selected for use by Faber et al.: (1) the spectrum of effective muscarinic receptor blockade was limited to only those alleviating gastrointestinal side effects; (2) the duration of action of the anticholinergic was too short for current practical use in highly non-compliant demented patients; (3) the anticholinergic given at maximum recommended doses can itself produce adverse effects which appear in addition to those of the AChEI; and (4) this report does not disclose or suggest that, by reducing adverse events, it might be possible to increase AChEI dose and thus improve efficacy.

In particular, concerning the problem (1) above, to the extent that propantheline targets gastrointestinal secretory and motility function and/or rather selectively blocks M1 receptors in the gastrointestinal tract, it would lack efficacy in mitigating many of the side effects of cholinesterase inhibitor therapies, by virtue of its limited ability to inhibit the effects of AChEI-induced stimulation of other muscarinic receptor subtypes, especially those of the M2 and M3 subtypes, located at various sites outside the CNS.

Hyperstimulation of peripheral M2 subtype muscarinic receptors, as occurs during AChEI treatment, contributes to such frequently occurring cardiovascular side effects as bradycardia, hypotension, palpitations, atrial fibrillation and other supraventricular cardiac conduction conditions. Any of these conditions could contribute to the occurrence of dizziness and syncope with AChEIs. Similarly, hyperstimulation of peripheral M3 subtype muscarinic receptors as occurs during AChEI treatment can also contribute to such frequently occurring side effects of AChEIs as hypotension, dizziness and syncope (due to vasodilation) as well as dyspnea (due to pulmonary bronchoconstriction), anorexia, dyspepsia, weight loss and abdominal cramps (due to increased intestinal motility); urinary incontinence (due to sphincter dilatation); and diaphoresis (due to exocrine gland hypersecretion). As noted by the above-cited article by Faber 1999, who used the maximum recommended dose, adverse effects of propantheline can commonly include tachycardia, constipation, blurred vision, dry mouth, and urinary retention. Each of these raise safety and tolerability issues and impair the quality of life of the elderly human beings that ordinarily manifest an Alzheimer type dementia.

Unfortunately, beside the problem of some drugs of this type having a short duration of action, drugs acting to block cholinergic transmission generally might mitigate cholinergic side effects, but would at the same time reduce the therapeutic benefit of AChEI therapy by virtue of their ability to block central cholinergic receptors. Indeed, anticholinergic drugs that enter the CNS are generally contraindicated in patients with Alzheimer type dementia in view of their potential to exacerbate cognitive dysfunction. In addition, they may cause, among various adverse effects noted especially in the elderly, dry mouth, pupillary dilatation with visual disturbances and risk of acute angle closure glaucoma, reduced bronchial secretions with an increased danger of pulmonary infection, diminished gastric secretions with impaired food absorption, reduced gastric motility with paralytic ileus, pseudo-obstruction and constipation, urinary retention, disorientation, agitation, hallucinations and delirium, cardiac conduction disturbances and supraventricular tachyarrhythmias, angina exacerbation and congestive heart failure, and thermoregulatory impairment.

U.S. Pat. No. 5,837,724 discloses a method for enhancing cognition comprising administration of the anticholinergic darifenacin, chemically 2-[1-[2-(2,3-dihydrobenzofuran-5-yl)ethyl]pyrrolidin-3-yl]-2,2-diphenyl-acetamide, and also discloses compositions comprising darifenacin and an AChEI, whereby the use of an AChEI in combination therapy may be particularly beneficial, and may have a synergistic effect. However, only a comparison of darifenacin with oxybutinin (without an AChEI) on patients with urge incontinence is provided by this document. In addition, darifenacin is a selective M3 antimuscarinic agent (C. R Chapple et al. Expert Opin Investig Drugs. 2004 November; 13(11):1493-500), such that the alleviation of the cholinergic side effects of AChEIs must be only partial by virtue of its limited ability to inhibit gastrointestinal and cardiac effects of stimulating M1 and, respectively, M2 subtype receptors located outside the CNS.

WO 2004/069246 discloses pharmaceutical compositions comprising AChEIs and anticholinergic muscarinic receptor blocking agents which cannot cross the blood-brain-barrier, said compositions being able to reduce gastro-intestinal side effects without reducing the treatment in senile dementia, thus widening the use of AChEIs for treating senile dementia. This document cites, as anticholinergic drugs, propantheline bromide, scopolamine methylbromide, isopropamide iodide, valethamate, scopolamine methobromide and methonitrate, atropine methonitrate, diponium bromide, pipenzolate bromide, penthienate bromide, benactizine methobromide and dibutoline sulfate, but the specifically described compositions are all made with propantheline bromide as anticholinergic agent, which, due to its short duration of action, is taken four times per day compared with the once or twice a day administration of the anticholinergic agents used according to the present invention and needed for the elderly, non compliant individuals suffering from dementias of Alzheimer type. In particular, the cited document neither discloses nor suggests that certain anticholinergic drugs may improve the treatment of Alzheimer type dementia, not only in terms of lessening of side effects but also in terms of increasing the efficacy on the symptoms of dementia.

Finally, in a series of documents A. K. Gunnar Aberg discloses the use of the anticholinergic trospium for treating urinary incontinence (US 2005/0043342, now U.S. Pat. No. 6,974,820), smooth muscle disorders in patients suffering from cardiac contractility disorders (US 2007/0004766) and smooth muscle disorders patients suffering from memory disorders (US 2006/0293356). According to this last document, smooth muscle disorders in patients suffering from a memory disorder may be treated with trospium while avoiding drug-induced memory disorders or drug-induced worsening of existing memory disorders. Even though this document states that the AChEIs have opposite effects to those of common anticholinergic drugs, it neither mentions nor suggests the possibility of improving the symptoms of Alzheimer type dementia by combining an AChEI and trospium.

After the Faber 1999 publication, other studies concerning the safety and the Brain-Blood-Barrier penetration capability of anticholinergic agents have been published.

For example, in an overview of the bladder dysfunction of dementia and Alzheimer's disease subjects, Schultz-Lampel, Urologe (A), 2003, 42, 1579-1587, illustrate the rationale of the diagnostic and the possibilities of therapy. Among other possible drug classes, the Author cites oxybutynine, propiverine, tolterodine and trospium chloride, the last one being capable of avoiding CNS complications. No AChEI is cited in this paper.

In a prospective randomized study, Takeda et al., 33rd Annu. Meet. Int. Continence Soc., 2003, 5-9 Oct., Abstract 166 ("Takeda 2003"), report the effects of the anticholinergics propiverine hydrochloride and oxybutinine hydrochloride on cognitive functions, urinary symptoms, urinary functions, and impact of caregiver in elderly dementia patients with urinary incontinence. AChEIs are not cited in this study. The Authors conclude that propiverine hydrochloride and oxybutinine hydrochloride had beneficial effects on both cognitive function and urinary incontinence as well as on the burden and quality of life of caregivers. No AChEI is cited in this document.

Scheifer et al., Clinical Therapeutics, 2004, 27(2), 144-153, describe the CNS adverse effects of anticholinergic drugs used for the treatment of the overactive bladder in the elderly. No AChEI is cited in this document.

In an overview of the anticholinergics currently prescribed in patients with overactive bladder (Der Urologe, 2006, 7, 830-833), H. Madersbacher spent particular attention to the influence of pharmacokinetics/pharmacodynamics on the adverse events profile including possible CNS side effects. In particular, according to this Author, tolterodine in combination with AChEIs has dramatically worsened the cognitive situation in geriatic patients by inducing delirious conditions which diminished after suspension of the treatment.

In a pharmacological study in mice using oral tolterodine, Cappon et al., Eur. J. Pharmacol., 2008, 579, 225-228, observed that the tested drug had no effect on memory in the mouse passive avoidance model and concluded that tolterodine does not disrupt cognitive function under the test conditions. No AChEI is cited in this document.

Siegler et al., Clin Parmacol Ther 2004; 75, 484-488 ("Siegler et al. 2004") studied the treatment of urinary incontinence with anticholinergics in patients taking cholinesterase inhibitors for dementia. The Authors conclude that it may be appropriate to prescribe anticholinergics and cholinesterase inhibitors together for patients with dementia who are troubled by the effects of detrusor instability and that the combination is an imperfect but often effective means of site-directed therapy in the absence of truly organ-specific medications.

In summary, the literature neither discloses nor suggests that advantage be taken of the side effect mitigation discovered by Faber 1999, achieved with propantheline and confirmed by further studies, to improve the magnitude and/or duration of the otherwise marginal therapeutic response to an AChEI, by allowing to increase the doses of said AChEI and concurrently improving neurobehavioral function and quality of life. No attempt was made in this direction heretofore.

Nevertheless there was and there continues to be an urgent need to enhance the dose regimen of AChEI in order to allow a substantive improvement in the symptoms of dementias of Alzheimer's type.

SUMMARY OF THE INVENTION

Considering the results of the above-cited previously published studies in animal models of human cognitive function indicating a dose-response relation between the amount of AChEIs and the degree of cognitive improvement achieved in the clinically relevant dose range, it has been assumed that if dose limiting side effects of AChEIs could be reduced or eliminated, then the administration of higher doses might provide a much needed increase the size of the therapeutic effect and prolong the duration of drug action, while at the same time having no significant deleterious effect on safety or tolerability.

The therapeutic approach according to the present invention reverses the approach taught by the prior art, in the sense that it provides for an increase of the therapeutic effect of the AChEI (i.e., increase in efficacy) by concurrently globally counteracting their side effects as opposed to combating their side effects without appreciably lessening the central activity of AchEIs, but without increasing their efficacy as taught by the prior art, in particular by WO 2004/069246.

Thus, it has been found that it is actually possible to maximize the effects of an AChEI in improving the symptoms of Alzheimer type dementia in a patient suffering from said symptoms by administering to said patient said AChEI in combination with a nsPAChA as defined above, i.e. with an anticholinergic agent that is largely, if not completely, excluded from the CNS, that will act with high affinity as a direct pharmacologic antagonist at all muscarinic acetylcholine receptors, at doses that are not likely to introduce additional side effects.

It has also surprisingly been found that by a combined nsPAChA/AChEI treatment, the maximization of the cholinomimetic efficacy is achieved with AChEI doses higher than the currently maximal tolerated ones and with nsPAChA doses equal to or even lower than those currently used for anticholinergic therapy, without onset of clinically significant cholinergic, peripheral adverse effects.

According to the present invention, pharmaceutical compositions comprising a pharmacologically active amount of an AChEI and a pharmacologically active amount of a nsPAChA, in admixture with pharmaceutical carriers, improve the symptoms of Alzheimer type dementia in patients suffering from said symptoms, even in the case of patients who have been withdrawn or are no longer responding to the AChEI therapy because of the severe side-effects, thus assuring not only an improvement of the quality of life of the patients, but also an objective and previously unrealized improvement of their symptoms.

DETAILED DESCRIPTION

The present invention proposes an improved method to augment the efficacy of conventional cholinergic therapies for Alzheimer type dementias by mitigating the common adverse events of cholinomimetic treatments of said Alzheimer type dementias that arise as a result of the concomitant stimulation of cholinergic receptors in the PNS. Drugs that act to selectively inhibit the activation of all the muscarinic receptors in the PNS, but not in the CNS, resulting from cholinomimetic therapy have the potential to reduce the adverse effects, such that higher cholinomimetic doses can be administered leading to higher and more prolonged antidementia efficacy with fewer peripherally mediated side effects. By combining an extended release cholinomimetic with a peripheral anticholinergic having an advantageous duration of pharmacologic action, in a single dosage form, the benefits to patients of an even longer duration of action is also achieved.

Thus, it is an object of the present invention to provide a method for increasing the maximal tolerated dose of an acetyl choline esterase inhibitor in a patient suffering from an Alzheimer type dementia without concurrent, appreciable adverse effects, which comprises administering to said patient said AChEI in combination with a non-selective, peripheral anticholinergic agent (nsPAChA), whereby an enhanced acetyl choline esterase inhibition in the CNS of said patient is achieved and the symptoms of an Alzheimer type dementia in said patient are improved.

The invention also provides the use of a non-selective, peripheral anticholinergic agent (nsPAChA) for the preparation of pharmaceutical compositions for the treatment of Alzheimer type dementias in combination with an AChEI, whereby the maximal tolerated dose of said AChEI is increased, a higher degree of acetyl choline esterase inhibition in the CNS is achieved and the symptoms of Alzheimer type dementia are improved to a greater extent without concurrent, appreciable adverse effects.

The efficacy of the nsPAChAs in improving the symptoms of Alzheimer type dementia is due to the fact that said nsPAChAs allow the increase of the therapeutic doses of all the AChEIs up to a factor of 4.

Advantageous AChEIs are those currently used or tested for this indication, such as 1,2,3,4-tetrahydro-9-acridinamine (tacrine), 9-amino-2,3,5,6,7,8-hexahydro-1H-cyclopenta[b] quinoline (ipidacrine); (±)-2,3-dihydro-5,6-dimethoxy-2-[[1-(phenylmethyl)-4-piperidinyl]methyl]-1H-inden-1-one (donepezil) and its pharmaceutically acceptable salts, in particular the hydrochloride, 3-[2-(1-benzyl-4-piperidyl)ethyl]-5,7,-dihydro-6H-pyrrolo[3,21]-1,2-benzisoxazol-6-one (icopezil) and its pharmaceutically acceptable salts, in particular the maleate, 3-[1-benzylpiperdin-4-yl]-1-(2,3,4,5-tetrahydro-1H-1-benzazepin-8-yl)propan-1-one (zanapezil) and its pharmaceutically acceptable salts, in particular the fumarate, (S)—N-Ethyl-N-methyl-3-[1-(dimethylamino)ethyl]-phenyl carbamate (rivastigmine) and its pharmaceutically acceptable salts, in particular the hydrogen (2R,3R)-tartrate, 4aS,6R,8aS-3-methoxy-11-methyl-4a,5,9,10,11,12-hexahydroxy-6H-benzofuro[3a,3,2-e,f]benzazepin-6-ol (galantamine); (1R,9S,13E)-1-amino-13-ethylidene-11-methyl-6-azatricyclo[7.3.1.0$^{2.7}$]trideca-2(7),3,10-trien-5-one (huperzine A) and phenserine and its analogs encompassed by the general formula I

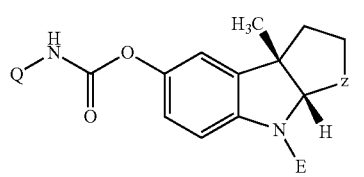

(I)

wherein Q is a phenyl group optionally substituted with a $(C_1-C_4)$alkyl or with a methoxy group, Z is an oxygen or sulfur atom or a N-E' radical, E and E', independently, are hydrogen or a methyl group optionally substituted with a phenyl or benzyl group.

Exemplary AChEIs of formula (I), described in U.S. Pat. No. 6,683,105, are phenserine (Q=phenyl; E=CH$_3$; Z=N—CH$_3$); (–)-N$^1$,N$^8$-bisnorphenserine (Q=phenyl; E=H; Z=N—H); 4'-methoxyphenserine (Q=4'-methoxyphenyl; E=CH$_3$; Z=N—CH$_3$); (–)-N$^1$,N$^8$-bisbenzylnorphenserine (Q=phenyl; E=CH$_2$C$_6$H$_5$; Z=N—CH$_2$C$_6$H$_5$); tolserine (Q=o-tolyl; E=CH$_3$; Z=N—CH$_3$); N'-benzylnortolserine (Q=o-tolyl; E=CH$_3$; Z=N—CH$_2$—C$_6$H$_5$); N$^1$-phenethylnortolserine (Q=o-tolyl; E=CH$_3$; Z=N—CH$_2$—CH$_2$—C$_6$H$_5$); N$^1$-nortolserine (Q=o-tolyl; E=CH$_3$; Z=N—H); N$^8$-benzylnortolserine (Q=o-tolyl; E=N—CH$_2$—C$_6$H$_5$; Z=N—CH$_3$); N$^8$-phenethylnortolserine (Q=o-tolyl; E=N—CH$_2$—CH$_2$—C$_6$H$_5$; Z=N—CH$_3$); N$^8$-nortolserine (Q=o-tolyl; E=H; Z=N—CH$_3$); N$^1$,N$^8$-bisnortolserine (Q=o-tolyl; E=H; Z=N—H); (–)-N$^1$,N$^8$-bisbenzylnortolserine (Q=o-tolyl; E=CH$_2$C$_6$H$_5$; Z=N—CH$_2$C$_6$H$_5$); cymserine (Q=p-isopropylphenyl; E=CH$_3$; Z=N—CH$_3$); N'-benzylnorcymserine (Q=p-isopropylphenyl; E=CH$_3$; Z=N—CH$_2$—C$_6$H$_5$); N$^1$-phenethylnorcymserine (Q=p-isopropylphenyl; E=CH$_3$; Z=N—CH$_2$—CH$_2$—C$_6$H$_5$); N'-norcymserine (Q=p-isopropylphenyl; E=CH$_3$; Z=N—H); N$^8$-benzylnorcymserine (Q=p-isopropylphenyl; E=N—CH$_2$—C$_6$H$_5$; Z=N—CH$_3$); N$^8$-phenethylnorcymserine (Q=p-isopropylphenyl; E=N—CH$_2$CH$_2$C$_6$H$_5$; Z=NCH$_3$); N$^8$-norcymserine (Q=p-isopropylphenyl; E=H; Z=N—CH$_3$); N$^1$,N$^8$-bisnorcymserine (Q=p-isopropylphenyl; E=H; Z=N—H); (–)-N$^1$,N$^8$-bisbenzylnorcymserine (Q=p-isopropylphenyl; E=CH$_2$C$_6$H$_5$; Z=N—CH$_2$C$_6$H$_5$); thiacymserine (Q=p-isopropylphenyl; E=CH$_3$; Z=S); thiatolserine (Q=o-tolyl; E=CH$_3$; Z=S).

Donepezil hydrochloride, rivastigmine hydrogen (2R,3R)-tartrate and galantamine are the preferred AIChEIs.

Advantageously, the used nsPAChAs are quaternary ammonium nsPAChAs, sulfonium nsPAChAs, (1S)-(3R)-1-azabicyclo[2.2.2]oct-3-yl 3,4-dihydro-1-phenyl-2(1H)-isoquinolinecarboxylate (solifenacin) and its pharmaceutically acceptable salts, 1-methylpiperidin-4-yl) 2,2-di(phenyl)-2-propoxyacetate(propiverine) and its pharmaceutically acceptable salts, 1,4,5,6-tetrahydro-1-methylpyrimidin-2-yl-methyl α-cyclohexyl-α-hydroxy-α-phenylacetate(oxyphencyclimine) and its pharmaceutically acceptable salts, (R)—N,N-diisopropyl-3-(2-hydroxy-5-methylphenyl)-3-phenylpropanamine (tolterodine) and its pharmaceutically acceptable salts. Said nsPAChAs, preferably, are compounds with a duration of action of at least 6 hours, advantageously from 8 to 24 hours, more advantageously from 10 to 24 hours, preferably from 12 to 24 hours, even though nsPAChAs having an appropriate duration of action corresponding to the duration of action of the concomitantly administered AChEI may be successfully used.

Particularly advantageous quaternary ammonium nsPAChAs or sulfonium nsPAChAs are compounds of formula II

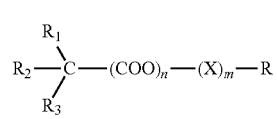

(II)

wherein
R is a radical selected from the group consisting of those of formulas (a)-(e)

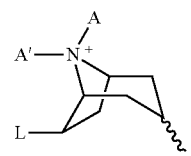

(a)

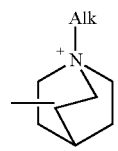

(b)

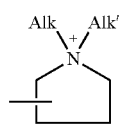

(c)

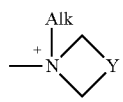

(d)

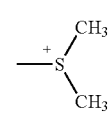

(e)

A being methyl and A' being $(C_1-C_4)$alkyl or 2-fluoroethyl group or A and A' forming a 1,4-butylene or 1,5-pentylene chain, L being hydrogen or methoxy, Alk and Alk' each being $(C_1-C_4)$alkyl and Y being a bivalent radical selected from the group consisting of 1,2-ethylene, 1,3-propylene, 1,4-butylene and 2-oxa-1,3-propylene; the corresponding counter ion being a pharmaceutically acceptable anion, such as a chloro, bromo, iodo, tartrate, hydrogen tartrate, succinate, maleate, fumarate, sulfate, hydrogen sulfate or methylsulfate anion;
n and m, independently, are zero or 1;
X is a $(C_2-C_3)$alkylene group;
$R_1$ and $R_2$ are each phenyl, cyclopentyl, cyclohexyl, 1-cyclohexenyl, 2-thienyl and, when R is a radical (a), also each represents $(C_1-C_4)$alkyl;

$R_3$ is H or OH or, only when R is a radical (a), also a COOAlk group, Alk being a ($C_1$-$C_4$)alkyl group.

Exemplary nsPAChAs of formula II above used for preparing medicaments for the treatment of Alzheimer type dementia in combination with AchEIs are

- anisotropine methylbromide [R=(a), A=A'=$CH_3$, L=H; n=1; m=0; $R_1$=$R_2$=n-$C_3H_7$; $R_3$=H;];
- ciclotropium bromide [R=(a), A=$CH_3$, A'=isopropyl, L=H; n=1; m=0; $R_1$=phenyl; $R_2$=cyclopentyl; $R_3$=H];
- flutropium bromide [R=(a), A=$CH_3$, A'=2-fluoroethyl, L=H; n=1; m=0; $R_1$=$R_2$=phenyl; $R_3$=OH];
- homatropine methylbromide [R=(a), A=A'=$CH_3$, L=H; n=1; m=0; R=phenyl; $R_2$=$R_3$=H];
- sintropium bromide; [R=(a), A=$CH_3$, A'=isopropyl, L=H; n=1; m=0; $R_1$=$R_2$=n-$C_3H_7$; $R_3$=H];
- tematropium metilsulfate [R=(a), A=A'=$CH_3$, L=H; n=1; m=0; $R_1$=phenyl; $R_2$=COO$C_2H_5$; $R_3$=H];
- tropenziline bromide [R=(a), A=A'=$CH_3$, L=methoxy; n=1; m=0; $R_1$=$R_2$=phenyl, $R_3$=OH];
- trospium chloride [R=(a), A+A'=1,4-butylene, L=H; n=1; m=0; $R_1$=$R_2$=phenyl; $R_3$=OH];
- clidinium bromide [R=(b)-3-, Alk=methyl; n=1; m=0; $R_1$=$R_2$=phenyl; $R_3$=OH];
- droclidinium bromide [R=(b)-3-, Alk=methyl; n=1; m=0; $R_1$=phenyl; $R_2$=cyclopentyl; $R_3$=OH];
- benzilonium bromide [R=(c)-3-, both Alk and Alk'=ethyl; n=1; m=0; $R_1$=$R_2$=phenyl; $R_3$=OH];
- benzopyrronium bromide [R=(c)-3-, both Alk and Alk'=methyl; n=1; m=0; $R_1$=$R_2$=phenyl; $R_3$=OH];
- cyclopyrronium bromide [R=(c)-3-, Alk=methyl and Alk'=ethyl; n=1; m=0; $R_1$=phenyl; $R_2$=cyclopentyl; $R_3$=H];
- glycopyrronium bromide (glycopyrrolate) [R=(c)-3-, both Alk and Alk'=methyl; n=1; m=0; $R_1$=phenyl; $R_2$=cyclopentyl; $R_3$=H];
- heteronium bromide [R=(c)-3-, both Alk and Alk'=methyl n=1; m=0; $R_1$=phenyl; $R_2$=2-thienyl; $R_3$=OH];
- hexopyrronium bromide [R=(c)-3-, both Alk and Alk'=methyl; n=1; m=0; $R_1$=phenyl; $R_2$=cyclohexyl; $R_3$=H];
- oxypyrronium bromide [R=(c)-2-, both Alk and Alk'=methyl; n=1; m=1; X=1,2-ethylene; $R_1$=phenyl; $R_2$=cyclohexyl; $R_3$=OH];
- ritropirronium bromide [R=(c)-3-, both Alk and Alk'=methyl; n=1; m=0; $R_1$=phenyl; $R_2$=cyclopentyl; $R_3$=OH];
- etipirium iodide [R=(d), Alk=methyl, Y=1,2-ethylene; n=1; m=1; X=1,2-ethylene; $R_1$=$R_2$=phenyl; $R_3$=OH];
- fenclexonium methylsulfate [R=(d), Alk=$CH_3$, Y=1,3-propylene; n=0; m=1; X=1,2-ethylene; $R_1$=phenyl; $R_2$=1-cyclohexenyl; $R_3$=H];
- tricyclamol chloride (procyclidine methochloride) [R=(d), Alk=methyl, Y=1,2-ethylene; n=0; m=1; X=1,2-ethylene; $R_1$=phenyl; $R_2$=cyclohexyl; $R_3$=OH];
- tiemonium iodide [R=(d), Alk=methyl, Y=2-oxa-1,3-propylene; n=0; m=1; X=1,2-ethylene; $R_1$=phenyl; $R_2$=2-thienyl; $R_3$=OH];
- hexasonium iodide [R=(e); n=1; m=1; X=1,2-ethylene; $R_1$=phenyl; $R_2$=cyclohexyl; $R_3$=H]; and
- oxysonium iodide [R=(e); n=1; m=1; X=1,2-ethylene; $R_1$=phenyl; $R_2$=cyclohexyl; $R_3$=OH.

Azoniaspiro[3β-benziloyloxy-(1α,5α-nortropane-8,1'-pyrrolidine]chloride (formula II, A+A'=1,4-butylene) described in U.S. Pat. No. 3,480,626, known under its International Non-proprietary Name trospium chloride, the tartrate, maleate, fumarate and succinate salts of trospium, solifenacin, described in U.S. Pat. No. 6,017,927 and the compound thereof with succinic acid, propiverine, described in DD 106643, and the hydrochloride thereof, oxyphencyclimine, described in GB 795758, and the hydrochloride thereof, tolterodine, described in U.S. Pat. No. 5,382,600, and the hydrogen tartrate thereof are the preferred nsPAChAs. Other pharmaceutical acceptable salts of trospium, in particular those with succinic and tartaric acids, are cited in US 2006/0293356. Trospium is a long-acting nsPAChA whose absorbed amount has an average plasma half life of about 18 hours.

The fact that nsPAChAs allow the increase of the maximal tolerated, therapeutic doses of the AChEIs from a randomized, controlled safety, tolerability, pharmacokinetic and pharmacodynamic study of an AChEI agent alone, such as rivastigmine, and with a nsPAChA, such as trospium chloride, in normal volunteers.

Standard approved oral dosage forms of both rivastigmine [as hydrogen-(2R,3R)-tartrate] and trospium chloride (simply named "trospium" in the study) are used. Trospium placebo tablets are essentially identical in appearance to standard trospium tablets. All drugs are administered orally, once daily in the morning.

The primary objective of the study is to determine the maximum tolerated dose (MTD) of the representative AChEI rivastigmine as monotherapy, i.e. when rivastigmine is administered alone orally at daily doses ranging from 3 mg to 36 mg, and as combination therapy, i.e. when rivastigmine is administered together with orally administered, representative nsPAChA trospium at daily doses of 20 or 40 mg.

The secondary objective of the study is to determine the ability of trospium to affect EEG activity when given with the MTD of rivastigmine.

This is a randomized, blinded, placebo-controlled, crossover and parallel groups, rising-dose, non-therapeutic study conducted on 36 subjects at a single center, during up to 14 days. Medical procedures including clinical history, physical examination, vital signs and laboratory tests are performed at screening, at regular prespecified intervals throughout the study, and at a follow up visit 7 days after last drug administration. An EEG is obtained 5 hours after administration of the first and last trospium dose. During the study, single daily doses of rivastigmine or rivastigmine placebo and trospium or trospium placebo are both administered orally at 8 AM. All subjects are maintained nothing per os (NPO) for the preceding 8 hours and until 4 hours after drug administration. Daily doses of rivastigmine hydrogen tartrate begin at 3 mg and may range up to 36 mg (in rivastigmine base) in small increments, as deemed clinically appropriate; daily doses of trospium begin at 20 mg and may increase to 40 mg, as clinically appropriate.

The subjects are aged 18 to 80 years, inclusive, who are considered in good general health. No concomitant medications are allowed, except those known to neither enter the central nervous system nor affect cholinergic function peripherally and given at stable doses throughout the study.

Safety and tolerability are evaluated based on clinical adverse experiences (AEs), vital signs (sitting systolic and diastolic blood pressure; radial pulse rate), 12-lead ECG, laboratory tests including urinalysis, and physical examination. Specifically in relation to rivastigmine AEs, the following are always evaluated: anorexia, nausea, vomiting. In relation to trospium AEs, the following are always evaluated: dry mouth, constipation, dyspepsia, abdominal pain, blurred vision, headache, dizziness, somnolence and confusion.

For pharmacokinetic evaluation, venous blood samples are drawn on Study Days when rivastigmine is given at its MTD as monotherapy and when rivastigmine is given at its MTD with trospium (nominally on Study Days 5 and 11) to measure serum concentrations of both drugs 75 minutes after their oral administration.

The analysis of primary and secondary objective measures is performed both in the intent-to-treat (ITT) population and in study completers. The ITT population includes all the randomized subjects who have received all baseline assessments and at least one post-randomization assessment.

For the intended use, the nsPAChA is formulated in pharmaceutical compositions comprising, as an active ingredient thereof, said nsPAChA in admixture with a pharmaceutical carrier.

The nsPAChA is present in an amount that reduces peripherally mediated adverse effects that would be caused by the administration of a dose of AChEI sufficient to maximally alleviate disease-associated dementia and other neurobehavioral symptoms.

Thus, according to another of its aspects, the present invention provides a pharmaceutical composition for inducing a higher acetyl choline esterase inhibition in the CNS of a patient suffering from Alzheimer type dementia, said patient taking a dose of acetyl choline esterase inhibitor (AChEI) higher than the maximal tolerated dose, comprising, as an active ingredient, a non-selective, peripheral anticholinergic agent (nsPAChA) in admixture with a pharmaceutical carrier. By such an induction of higher acetyl choline esterase inhibition, not otherwise attainable when AChEIs are taken alone, the symptoms of Alzheimer type dementia in said patients are thus further improved.

Advantageously, these pharmaceutical compositions comprise the nsPAChA active ingredient in an amount of from 20% to 200% of the dosage used in the compositions currently used for the treatment of disorders such as gastrointestinal cramping, bladder spasms, asthma, motion sickness, muscular spasms, and smooth muscle contractive disorders. The compositions prepared using the nsPAChAs according to the present invention allow the administration of 1.5- up to 4-times the maximal tolerated dose of AChEI to patients suffering of Alzheimer type dementia without clinically significant symptoms of peripheral cholinergic system overstimulation.

The compositions are preferably formulated in dosage unit forms for oral or parenteral, in particular transdermic, administration, wherein the active ingredient is mixed with a pharmaceutical carrier.

The pharmaceutical compositions prepared using the nsPAChAs according to the present invention are indicated in the treatment of the symptoms of Alzheimer type dementias in order to improve to a greater extent said symptoms by allowing an increase of the currently used doses of an AChEI, concurrently or sequentially administered therewith, without the side-effects that would hinder said increase of said therapeutic doses.

Preferred pharmaceutical compositions for oral administration using trospium chloride as preferred active ingredient may contain from 4 to 40 mg, preferably from 10 to 40 mg, of said active ingredient in IR formulations or from 15 to 120 mg, preferably from 30 to 120 mg, in ER formulations. Said preferred pharmaceutical compositions allow the concurrent or sequential administration of, for example, from 5 to 40 mg of donepezil hydrochloride, from 3 to 20 mg of rivastigmine tartrate or from 8 to 40 mg of galantamine without appreciable side-effects.

According to an advantageous embodiment, the pharmaceutical compositions prepared by using the nsPAChAs according to the present invention are present in unit forms also containing other active ingredients, in particular an AChEI which acts as cholinergic agent in the CNS to improve the symptoms of Alzheimer type dementia, in a quantity sufficient to maximally alleviate disease-associated neurobehavioral symptoms, with minimum of treatment-associated adverse effects.

Thus, it is another object of the present invention to provide a pharmaceutical unit form which comprises
(a) a nsPAChA selected from the group consisting of solifenacin, pharmaceutically acceptable salts of solifenacin, propiverine, pharmaceutically acceptable salts of propiverine, oxyphencyclimine, pharmaceutically acceptable salts of oxyphencyclimine, tolterodine, pharmaceutically acceptable salts of tolterodine and quarternary ammonium or sulfonium compounds of formula II

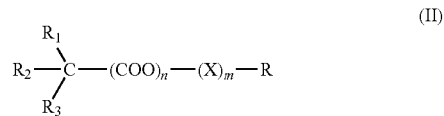

wherein
R is a radical selected from the group consisting of those of formulas (a)-(e)

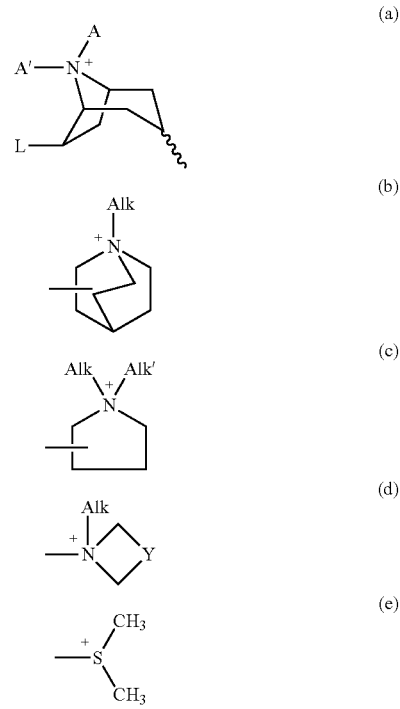

A being methyl and A' being $(C_1-C_4)$alkyl or 2-fluoroethyl group or A and A' forming a 1,4-butylene or 1,5-pentylene chain, L being hydrogen or methoxy, Alk and Alk' each being $(C_1-C_4)$alkyl and Y being a bivalent radical selected from the group consisting of 1,2-ethylene, 1,3-propylene, 1,4-butylene and 2-oxa-1,3-propylene; the corresponding counter ion being a pharmaceutically acceptable anion;
n and m, independently, are zero or 1;
X is a $(C_2-C_3)$alkylene group;
$R_1$ and $R_2$ are each phenyl, cyclopentyl, cyclohexyl, 1-cyclohexenyl, 2-thienyl and, when R is a radical (a), also each represents $(C_1-C_4)$alkyl;

R₃ is H or OH or, only when R is a radical (a), also a COOAlk group, Alk being a (C₁-C₄)alkyl group; and
(b) an AChEI;
in admixture with at least a pharmaceutical carrier.

The pharmaceutical composition to improve the treatment of human dementias of the Alzheimer type according to the present invention may comprise a mixture of a nsPAChA [component (a)] and of an AChEI [component (b)], wherein component (b) is present in a quantity sufficient to maximally alleviate disease-associated neurobehavioral symptoms and wherein component (a), which does not appreciably penetrate the blood brain barriers, is present in a second quantity that reduces peripherally mediated adverse effects that would be caused by the AChEI if administered without the accompanying nsPAChA.

Advantageous nsPAChAs are solifenacin and its salts, propiverine and its salts, oxyphencyclimine and its salts and quaternary ammonium salts or sulfonium salts of formula II above, such as homatropine quaternary salts, anisotropine quaternary salts, trospium quaternary salts, clidinium quaternary salts, benzilonium quaternary salts and glycopyrronium quaternary salts.

Preferred component (a) is a pharmaceutically acceptable salt of trospium, especially trospium chloride, succinate, maleate, fumarate or tartrate, a pharmaceutically acceptable salt of solifenacin, especially its compound with succinic acid 1:1, a pharmaceutically acceptable salt of propiverine, especially its hydrochloride, a pharmaceutically acceptable salt of oxyphencyclimine, especially its hydrochloride or a pharmaceutically acceptable salt of tolterodine, especially its L-hydrogen tartrate.

Advantageous components (b) are 1,2,3,4-tetrahydro-9-acridinamine (tacrine), 9-amino-2,3,5,6,7,8-hexahydro-1H-cyclopenta[b]quinoline (ipidacrine); (±)-2,3-dihydro-5,6-dimethoxy-2-[[1-(phenylmethyl)-4-piperidinyl]methyl]-1H-inden-1-one (donepezil) and its pharmaceutically acceptable salts, (S)—N-Ethyl-N-methyl-3-[1-(dimethylamino)ethyl]-phenyl carbamate (rivastigmine) and its pharmaceutically acceptable salts, 4aS,6R,8aS-3-methoxy-11-methyl-4a,5,9,10,11,12-hexahydroxy-6H-benzofuro[3a,3,2-e,f]benzazepin-6-ol (galantamine); (1R,9S,13E)-1-amino-13-ethylidene-11-methyl-6-azatricyclo[7.3.1.0²·⁷]trideca-2(7),3,10-trien-5-one (huperzine A) and phenserine and its analogs encompassed by the general formula I.

Advantageous AChEIs include those now part of standard care for patients suffering from a dementia of the Alzheimer type and that are also widely used off-label for various other chronic progressive disorders of cognitive function. AChEIs have as a general mechanism of action the enhancement of acetylcholine-mediated neurotransmission. All act in the human CNS to increase and prolong the availability of acetylcholine by inhibiting its degradatory enzyme acetylcholinesterase, such as donepezil; pharmaceutically acceptable salts of donepezil, especially the hydrochloride thereof; icopezil, pharmaceutically acceptable salts of icopezil, especially the maleate thereof, zanapezil, pharmaceutically acceptable salts of zanapezil, especially the fumarate thereof, rivastigmine; pharmaceutically acceptable salts of rivastigmine, especially the hydrogen tartrate thereof; galantamine; pharmaceutically acceptable salts of galantamine; Huperzine A.

Preferred component (b) is an AChEI selected from the group consisting of tacrine; huperzine A, donepezil hydrochloride; the hydrogen-(2R,3R)-tartrate of rivastigmine (rivastigmine tartrate); galantamine, the last three compounds being particularly preferred. As set forth above, these AChEIs vary in their pharmacological profiles and in their affinities for AChE and butyrylcholinesterase.

The dose of the component (b) may vary according to intrinsic acetylcholine esterase inhibiting potency of said component. Advantageously, said dose is from 1.5-fold to 4-times higher than the maximal tolerated one currently used when the same AChEI is administered alone.

In the unit forms of the present invention, for immediate release or extended release, the nsPAChA component (a) is present in an amount of from 20% to 600% of the amount of said nsPAChA contained in the currently administered IR dosage unit forms for the treatment of disorders such as gastrointestinal cramps, urinary bladder spasm, asthma, motion sickness, muscular spasms and the AChEI component (b) is present in an amount of from 100% to 600% of the amount of said AChEI contained in the currently administered IR dosage unit forms for the treatment of Alzheimer type dementia.

More particularly, the nsPAChA is present, in an IR unit form, in an amount ranging from 20% to 200% of the amount of said nsPAChA contained in the currently administered IR dosage unit forms for the treatment of the above-cited disorders or, in an ER unit form, in an amount ranging from 75% to 600% of the amount of said nsPAChA contained in the currently administered unit dosage IR forms for the treatment of the above-cited disorders. For example, trospium chloride, which is a preferred anticholinergic agent used as component (a), is present in an amount of from 4 mg to 120 mg per dosage unit, in particular from about 4 to about 40 mg, preferably from 10 to 40 mg, per dosage unit in an IR unit form or in an amount of from 15 to 120 mg, preferably from 30 to 120 mg, in an ER unit form, i.e. in amount of from 20% to 600% of the amount of trospium chloride which is present in IR unit forms for the treatment of overactive bladder.

In unit form for immediate release or extended release, the AChEI component (b) is present in an amount of from about 100% to about 600% of the amount of said AChEI contained in the currently administered IR dosage unit forms for the treatment of Alzheimer type dementia.

More particularly, the AChEI component (b) is present in an IR unit form, in an amount ranging from about 100% to about 400%, preferably from 150% to 400%, of the amount of said AChEI contained in the currently administered IR dosage unit forms for the palliative treatment of Alzheimer type dementia or, in an ER unit form, in an amount ranging from 150% to 600%, preferably from 200% to 600%, of the amount of said AChEI contained in the currently administered unit dosage IR forms for the treatment of Alzheimer type dementia. For example, among the preferred components (b), donepezil hydrochloride is present in an amount of from 5 mg to 60 mg, preferably from 7.5 to 60 mg, per dosage unit, rivastigmine, as the hydrogen tartrate thereof, is present in an amount of from 1.5 mg to 36 mg, preferably from 2.25 mg to 36 mg per dose unit, galantamine is present in an amount of from 4 to 72 mg per dose unit. Huperzine A is present in an amount of from 100 μg to 1.2 mg, preferably from 150 μg to 1.2 mg per dose unit.

Advantageously, said AChEI can be administered in a dose that is higher than the maximal tolerated dose of the same AChEI when administered alone and will preferably be from 1.5 to 4 times higher than the currently recommended doses in the treatment of Alzheimer type dementia.

The unit form of the present invention may be a tablet, a capsule, a pre-measured volume of a liquid solution or suspension for oral administration or a patch for transdermal application. In said unit form the nsPAChA and the AChEI may be mixed together or separated according to known technologies in admixture with a pharmaceutical carrier in a pharmaceutical composition.

Component (a) and component (b) are formulated with conventional pharmaceutical carriers in known formulations for oral use wherein said components are mixed together or separated, for example in two tablets introduced in a capsule or in a two-compartment capsule or in a multilayer (di-layer) tablet wherein the two components are both in IR or in ER form or one of the two components is in IR form and the other is in ER form, according to known technologies.

The pharmaceutical carriers and vehicles are those commonly used for the preparation of compositions for oral, buccal and parenteral, in particular transdermal, administration. Appropriate unit forms comprise the oral forms such as tablets, soft or hard gelatine capsules, powders or granulates in sachets and suitably measured oral solutions or suspensions as well as patches for transdermal administration.

Component (a) and component (b) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a) and component (b) may also be formulated in the form of microcapsules, optionally with one or more carriers or additives.

For oral administration, component (a) and component (b), together or separately, are formulated by mixing the active ingredient with conventional pharmaceutical acceptable carriers enabling said active ingredients to be formulated in tablets, dragees, orally disintegrating tablets, capsules, liquid solutions or suspensions, syrups and the like.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubricants such as polyethyleneglycol or magnesium stearate; ligands such as methylcellulose, sodium carboxymethylcellulose, alginic acid, alginates; sweeteners, such as saccharose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of components (a) and (b) such as sorbitol, mannitol, lactose and cellulose.

Carriers for liquid, normally aqueous, suspensions or solutions include for example antioxidants, such as sodium metabisulfite or sodium sulfite, thickening agents, such as microcrystalline cellulose, hydroxypropylcellulose, carboxymethylcellulose or polyvinylpyrrolidone, preservatives such as methyl paraben, ethyl paraben, sodium ethylenediaminotetracetate, sodium benzoate or an alkaline salt of sorbic acid, as well as flavoring and sweetening agents.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

The composition according to the present invention may be in form of a capsule containing two tablets as described herein above, one of them comprising component (a) and the other comprising component (b).

The association nsPAChA/AChEI may be formulated in tablets in which one or both of the two components is in controlled-release formulation, for example as a dispersion of said component in hydroxypropyl methyl cellulose or in a film-coated microgranule. Advantageously, the AChEI, in a ER-formulation is in the core and the nsPAChA, in IR-formulation, is in the outer layer in multi-layer tablets in which, for example, both the core and the outer layer are coated with a film. Analogously, capsules made of two separated parts, one containing component (a), in IR- or ER-formulation and the other containing component (b), in IR- or ER-formulation, may be used Carriers and vehicles for ER tablets include retardant materials such as is acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

In particular, the unit forms of the present invention comprise a pharmaceutically acceptable salt of trospium as a nsPAChA and a member selected from the group consisting of tacrine, in an amount of from 10 mg to 160 mg, donepezil and its pharmaceutically acceptable salts, in an amount of from 5 mg to 40 mg, rivastigmine and its pharmaceutically acceptable salts, in an amount of from 1.5 to 36 mg, galantamine, in an amount of from 4 to 48 mg, and huperzine A, in an amount of from 100 µg to 1.2 mg as an AChEI.

According to an embodiment, the compositions of the present invention are formulated by mixing the component (a) and the component (b) together, in admixture with a pharmaceutical carrier for an immediate or extended release. An advantageous composition according to this embodiment comprises from 4 to 40 mg of trospium chloride, as component (a); and from 5 to 50 mg of donepezil (as hydrochloride); or
from 1.5 to 30 mg of rivastigmine (as hydrogen tartrate); or
from 4 to 60 mg of galantamine, as component (b), wherein components (a) and (b) are mixed together and with a pharmaceutical carrier in an IR-formulation, said composition being destined to be administered once or twice per day.

According to another embodiment, the compositions of the present invention are formulated by mixing the component (a) with a pharmaceutical carrier for an immediate or extended release in tablets (Tablet A) and the component (b), separately, with a pharmaceutical carrier for an immediate or extended release in tablets (Tablet B) and introducing Tablet A and Tablet B in a capsule for oral administration as described for example in GB 1204580 or in US 2007/0224259. An advantageous composition according to this embodiment consists of soft or hard gelatine capsules each containing Tablet A comprising from 4 to 40 mg of trospium chloride, as component (a); in admixture with a pharmaceutical carrier in a IR formulation; and Tablet B, comprising
from 5 to 50 mg of donepezil (as hydrochloride); or
from 1.5 to 30 mg of rivastigmine (as hydrogen tartrate); or
from 4 to 50 mg of galantamine, as component (b), with a pharmaceutical carrier in an IR-formulation said composition being destined to be administered once or twice per day.

According to a further embodiment, the compositions according to the present invention are formulated in a di-layer tablet which releases two drug doses, in which the release of a drug from one drug-containing layer does not interfere with the release of a drug from the other drug-containing layer as described for example in WO 2006/089493. An advantageous composition according to this embodiment consists of
Layer A, comprising from 4 to 40 mg of trospium chloride, as component (a), with a pharmaceutical carrier in a IR formulation and
Layer B, comprising 4 to 60 mg of galantamine,
as component (b), in admixture with a pharmaceutical carrier in an IR-formulation, said composition being destined to be administered once or twice per day.

According to another embodiment, the compositions of the present invention are formulated in oral disintegrable tablets. Particularly advantageous compositions according to this embodiment are orally disintegrable tablets comprising
from 4 to 40 mg of trospium chloride, as component (a); and
from 5 to 50 mg of donepezil hydrochloride, as component (b),
in admixture with a pharmaceutical carrier in an IR-formulation for buccal mucosa absorption, said composition being destined to be administered once per day.

According to another embodiment, the compositions of the present invention are formulated in solutions for oral administration wherein component (a) and component (b) are dissolved or suspended in water in admixture with conventional carrier or vehicles. Particularly advantageous compositions according to this embodiment are oral solutions or suspensions comprising
from 4 to 40 mg of trospium chloride, as component (a); and
from 4 to 50 mg of galantamine, as component (b),
in admixture with a pharmaceutical carrier in a liquid IR-formulation for oral administration, said composition being destined to be administered once or twice per day.

According to another embodiment, the compositions of the present invention are formulated in patch for transdermal administration. Particularly advantageous compositions according to this embodiment are transdermal patch formulations comprising
from 4 mg/24 hours to 120 mg/24 hours of trospium chloride, as component (a); and
from 4.6 mg/24 hours to 30 mg/24 hours of rivastigmine (as hydrogen tartrate), as component (b),
with a pharmaceutically acceptable carrier or diluent which is suitable for systemic transdermal administration.

Another embodiment of the present invention provide units forms consisting of tablets comprising
from 5 to 15 mg of solifenacin succinate, as component (a); and
from 4 to 50 mg of galantamine, as component (b),
in admixture with a pharmaceutical carrier in a IR-formulation for oral administration, said composition being destined to be administered once or twice per day.

As compared to known drugs of the acetylcholine esterase inhibitor type now used alone in the treatment of Alzheimer type dementias, the above combined pharmaceutical composition shows greater and longer efficacy and less adverse effects by allowing the safe and tolerable administration of larger and thus more therapeutically effective quantities of said acetylcholine esterase inhibitor. In particular, the acetylcholine esterase inhibitor of the pharmaceutical compositions of the present invention is safe and effective, alone or in combination with other pharmaceuticals, in treating patients in need of an acetylcholine esterase inhibition, in particular dementias of the Alzheimer type on a once or twice daily basis.

The pathologic conditions treated with the composition of the present invention include, but are not limited to, Alzheimer's disease, Parkinson's disease dementia, and other disorders of human cognitive and neurobehavioral function that are treated, in part, by pharmaceuticals intended to augment brain acetylcholine-mediated neurotransmission.

The therapeutic efficacy is measured by the degree to which cognitive and other neurobehavioral disabilities associated with dementias of the Alzheimer type, as documented by the use of standard scales, are reduced.

The following examples illustrate the invention.

EXAMPLE 1

Orally Disintegrating Tablets Containing 15 mg of Donepezil Hydrochloride and 20 mg of Trospium Chloride.

One and a half kilogram of donepezil hydrochloride and 1.8 kg of corn starch are mixed thoroughly until complete homogenizing of the mixture which, after a passage through a 35 mesh sieve, is added with a previously prepared mixture of 2 kg of trospium chloride, thoroughly stirred together with 2.4 kg of corn starch and sieved at 35 mesh. The mixture thus obtained is added with 0.6 kg of strawberry flavor powder, 0.2 kg of sodium saccharin, 13.08 kg of lactose, 4.4 kg of microcrystalline cellulose, and 2.9 kg of sorbitol. The mixture is mixed until complete homogenization, then it is added with 0.1 kg of magnesium stearate, mixed again and compressed with punches of 7 mm to obtain 100,000 orally disintegrating tablets having the following composition

| | |
|---|---|
| Donepezil hydrochloride | 15.00 mg |
| Trospium chloride | 20.00 mg |
| Corn starch | 42.00 mg |
| Strawberry flavor powder | 6.00 mg |
| Sodium saccharin | 2.00 mg |
| Lactose | 130.00 mg |
| Microcrystalline cellulose | 44.00 mg |
| Sorbitol | 29.00 mg |
| Magnesium stearate | 1.00 mg |

EXAMPLE 2

Capsules for oral administration are prepared by mixing the following ingredients:

| Ingredients | Parts by weight |
|---|---|
| Rivastigmine (as hydrogen tartrate) | 900 |
| Trospium chloride | 2.000 |
| Lactose USP | 7.350 |
| Colloidal silicon dioxide (Aerosil ®) | 50 |

After mixing, the mixture is screened through a 40 mesh screen and introduced in two-piece hard gelatine capsule No. 3 containing 9 mg of rivastigmine and 20 mg of trospium chloride

EXAMPLE 3

Immediate release tablets for oral administration are prepared by mixing 1.8 kg of galantamine and 2.0 kg of trospium chloride, 0.25 kg of gelatin, 0.25 kg of magnesium stearate and 10 kg of corn starch and forming the mixture into tablets containing 18 mg of galantamine and 20 mg of trospium chloride by a conventional tableting machine.

EXAMPLE 4

An oral liquid composition is prepared in a blender equipped with a blade stirrer, wherein 1800 g of galantamine and 5 kg of deionized water are added. The temperature is maintained at 40° C. and the mixture is vigorously stirred until complete solution. The temperature is brought to 25° C., then 20.22 g of potassium sorbate, 44.11 g of sodium metabisulfite and 147 g of commercial strawberry flavoring agent are added. Stirring is continued at room temperature until a clear solution is obtained. The temperature of the obtained solution is brought to 20° C. and added with a previously prepared solution containing 2757 g of xylitol, 2000 g of trospium chloride and 18.38 g of microcrystalline cellulose in 4.41 kg of deionized water. After a gentle stirring to obtain a complete dispersion, the solution thus obtained is passed through a sieve 1.5 mesh. Thus, about 15 kg of a solution are obtained, to be introduced in 1500 unit doses of the following composition

| Galantamine | 18.00 mg |
|---|---|
| Trospium chloride | 20.00 mg |
| Sodium metabisulfite | 4.40 mg |
| Potassium sorbate | 2.02 mg |
| Xylitol C | 27.57 mg |
| Strawberry flavoring agent | 80.00 mg |
| Microcrystalline cellulose | 10.00 mg |
| Deionized water to | 10,000.00 mg |

EXAMPLE 5

Tablets containing 4 mg of galantamine formulated with a pharmaceutical carrier, tablets containing 12 mg of galantamine formulated with a pharmaceutical carrier and tablets containing 20 mg of trospium chloride formulated with a pharmaceutical carrier are distributed in capsules as described in GB 1,254,580, such that unit dosage forms containing 16 mg of galantamine and 20 mg of trospium are prepared. In the same manner, unit dosage forms containing 8 mg of galantamine formulated with a pharmaceutical carrier, tablets containing 20 mg of galantamine formulated with a pharmaceutical carrier and tablets containing 20 mg of trospium chloride formulated with a pharmaceutical carrier are prepared.

EXAMPLE 6

By operating as described in Example 1, but using 1.5 Kg of propiverine hydrochloride instead of 2 Kg of trospium chloride, orally disintegrating tablets having the following composition are obtained

| Donepezil hydrochloride | 15.00 mg |
|---|---|
| Propiverin hydrochloride | 15.00 mg |
| Corn starch | 42.00 mg |
| Strawberry flavor powder | 6.00 mg |
| Sodium saccharin | 2.00 mg |
| Lactose | 130.00 mg |
| Microcrystalline cellulose | 44.00 mg |

-continued

| Sorbitol | 29.00 mg |
|---|---|
| Magnesium stearate | 1.00 mg |

The invention claimed is:

1. A method for increasing the therapeutic effect of an acetyl choline esterase inhibitor (AChEI) in a patient suffering from an Alzheimer type dementia, which comprises administering to said patient said AChEI selected from the group consisting of tacrine, donepezil, rivastigmine, galantamine, and pharmaceutically acceptable salts thereof, at a dose level from 1.5 to 4 times greater than a recommended maximal dose level approved by the U.S. FDA, in combination with a non-selective, peripheral muscarinic anticholinergic agent (nsPAChA).

2. The method of claim 1, wherein said AChEI is administered to said patient concurrently or sequentially with said nsPAChA, whereby an enhanced acetyl choline esterase inhibition in the CNS of said patient is achieved and the symptoms of an Alzheimer type dementia in said patient are improved.

3. The method of claim 1, wherein said nsPAChA is formulated in a pharmaceutical composition, in admixture with a pharmaceutical carrier, in an amount of from 20% to 200% of the dosage used in compositions currently used for anticholinergic therapy.

4. The method of claim 1, wherein said pharmaceutical composition containing the nsPAChA is in a unit form also containing an AChEI.

5. The method of claim 4, wherein said unit farm is an IR unit form in which said nsPAChA is present in an amount ranging from 20% to 200% of the amount of said nsPAChA contained in the currently administered IR dosage unit forms for anticholinergic therapy.

6. The method of claim 4, wherein said unit form is an ER unit form in which said nsPAChA is present in an amount ranging from 75% to 600% of the amount of said nsPAChA contained in the currently administered IR dosage unit forms for anticholinergic therapy.

7. The method of claim 1, wherein said nsPAChA is selected from the group consisting of quaternary ammonium nsPAChAs, sulfonium nsPAChAs, (1S)-(3R)-1-azabicyclo [2.2 0]oct-3-yl 3,4-dihydro-1-phenyl-2(1H)-iso-quinolinecarboxylate (solifenacin) and its pharmaceutically acceptable salts, 1-methylpiperidin-4-yl) 2,2-di(phenyl)-2-propoxyacetate (propiverine) and its pharmaceutically acceptable salts, 1,4,5,6-tetrahydro-1-methylpyrimidin-2-yl-methyl α-cyclohexyl-α-hydroxy-α-phenylacetate (oxyphencyclimine) and its pharmaceutically acceptable salts, (R)—N,N-diisopropyl-3-(2-hydroxy-5-methylphenyl)-3-phenylpropanamine (tolterodine) and its pharmaceutically acceptable salts.

8. The method of claim 7 wherein said nsPAChA is selected from the group consisting of pharmaceutically acceptable salts of azoniaspiro[3β-benziloyloxy-(1α,5α)-nortropane-8, 1'-pyrrolidine](trospium), solifenacin and the compound thereof with succinic acid, propiverine and the hydrochloride thereof, oxyphencyclimine and the hydrochloride thereof, tolterodine and the hydrogen tartrate thereof.

9. The method of claim 1, wherein said nsPAChA is selected from the group consisting of trospium pharmaceutically acceptable salts; solifenacin and pharmaceutically acceptable salts thereof; propiverine and pharmaceutically acceptable salts thereof; and said AChEI is selected from the group consisting of donepezil and pharmaceutically acceptable salts thereof; rivastigmine and pharmaceutically acceptable salts thereof; and galantamine and pharmaceutically acceptable salts thereof.

10. A method for increasing the therapeutic dose of donepezil or pharmaceutically acceptable salts thereof in a patient suffering from an Alzheimer type dementia, which comprises administering to said patient said donepezil in combination with solifenacin or pharmaceutically acceptable salts thereof, wherein said donepezil is administered to said patient at a dose from 1.5 to 4 times greater than a recommended maximal dose level approved by the U.S. FDA.

11. The method of claim 10, wherein said patient is administered donepezil hydrochloride and solifenacin succinate.

12. The method of claim 11, wherein said donepezil is administered in a pharmaceutical composition in which said donepezil is present in an amount of from 15 mg to 60 mg.

13. The method of claim 11, wherein said donepezil is administered at a daily dose of from 15 mg to 40 mg.

* * * * *